United States Patent [19]
Israel

[11] Patent Number: 5,121,745
[45] Date of Patent: Jun. 16, 1992

[54] SELF-INFLATABLE RESCUE MASK

[76] Inventor: Michael B. Israel, 94 Pantigo Rd., East Hampton, N.Y. 11937

[21] Appl. No.: 555,844

[22] Filed: Jul. 23, 1990

[51] Int. Cl.$^5$ .................................... A61M 16/00
[52] U.S. Cl. .......................... 128/202.28; 128/203.11
[58] Field of Search ................ 128/202.28, 202.29, 128/203.11, 206.24, 206.26

[56] References Cited

U.S. PATENT DOCUMENTS

| | | | |
|---|---|---|---|
| 2,254,854 | 9/1941 | O'Connell | 128/206.26 |
| 2,875,757 | 3/1959 | Galleher, Jr. | 128/206.26 |
| 2,887,104 | 5/1959 | Sovinsky et al. | 128/203.11 |
| 4,062,357 | 12/1977 | Laerdal | 128/206.26 |
| 4,337,767 | 7/1982 | Yahata | 128/206.26 |
| 4,811,730 | 3/1989 | Milano | 128/203.11 |
| 4,834,085 | 5/1989 | Webster, II | 128/203.11 |

Primary Examiner—Edgar S. Burr
Assistant Examiner—Aaron J. Lewis
Attorney, Agent, or Firm—Edith Grill

[57] ABSTRACT

A disposable self-inflatable rescue mask for ventilation CPR (cardio-pulmonary resuscitation) comprising a transparent, flexible form-retaining plastic dome-shaped foldable portion having around its peripheral edge an inflatable bladder provided wtih a built-in self-sealing air valve, which allows the ambient air to flow into the inflatable bladder and self-seals the air in the self-inflated mask which retains its shape firmly, said bladder being shaped to fit around the nose and mouth areas, and effectively seal against the patient's face; and a blow-in tube disposed in an opening at the apex of the dome is provided with a mouthpiece for delivery of expired air to the patient.

The mask is packaged in a carrying case comprising two similar parts to form a container which is shaped to receive said deflated mask in a flattened and folded state, and sealed with a closure means.

17 Claims, 3 Drawing Sheets

SELF-INFLATABLE RESCUE MASK

BACKGROUND OF THE INVENTION

The present invention relates to a compactly packaged, disposable, self-inflatable rescue mask, which self inflates when removed from the package, useful for instant delivery of expired air to a victim's mouth and nose, without risk of physical contact and contamination from communicable diseases.

There is a great need for a disposable hygiene resuscitation device to avoid the risk of physical contact and contamination from communicable diseases such as herpes, hepatitis, tuberculosis, AIDS, etc., when administering C.P.R. (cardio-pulmonary resuscitation). There is also a need for portable packages of a disposable resuscitation device for instant use in emergencies. The American Heart Association states that mouth to mask ventilation is the most efficient and preferred method of administering artificial ventilation.

Various prior art disposable resuscitation devices have been developed to transfer air from the mouth of the rescuer into the mouth of the patient without direct contact with the patient. G.B. Patent No. 2,198,957A discloses a disposable mouth-to-mouth resuscitation device comprising a one piece molded mask with built in air seals on the underside of the mask, and an air inflation tube which passes through the mask and is placed between the teeth in the patient's mouth. The rescuer blows air into the outer end of said tube which flows into the patient's mouth, and simultaneously presses downward on both sides of the patient's cheeks. This pressure can lead to painful compression areas.

U.S. Pat. No. 3,802,428 discloses another disposable mouth-to-mouth resuscitation device comprising a central opening in a face mask provided with a flexible tubular extension, which is placed into the mouth of the victim. The rescuer secures the mask over his face by means of flexible straps, and blows air through said central opening into the flexible tubular extension placed in the patient's mouth. The resuscitator applies pressure to the victim's nostrils and holds the victims jaws and head in the proper position and forms a seal around the mouth of the victim with his own lips. This pressure and manipulation of the patient can lead to painful compression areas.

U.S. Pat. No. 4,579,114 discloses another disposable mouth to mouth resuscitation device including a flexible air tube provided with a resuscitator mouth piece at one end, and a one-way valve at the patient's end of the air tube which is secured to a mask held down by the hand of the resuscitator on the mouth and nose of the victim. Said one-way valve prevents movement of air or other fluid in the flexible air tube, to protect the resuscitator from contaminated liquids exhaled by the victim. This device also requires pressure on the victim's face.

In order to overcome the use of folded masks that require pressure and/or manipulation of the patient's face and/or head which causes painful compression areas, the Laerdal Canadian Patent 960003 (British Patent 1,318,378) disclosed a dome shaped foldable mask, which fits over the patient's nose and mouth and has an inlet tube for a gas source or for mouth to mouth resuscitation. A rim on the face side of the mask forms an inflatable flexible band which holds the mask in place and firmly shaped. When deflated, the mask can be packed flat in a small space, in order to overcome the difficulties encountered with rigid dome masks. However, the time spent inflating the band into a resuscitation mask is crucial, especially in emergencies.

None of the above cited art discloses a disposable, self-inflatable rescue mask, which provides a tight mask-to-face seal on the patient and instant delivery of expired air from the rescuer to the victim's mouth and nose in respiratory arrest emergencies.

SUMMARY OF THE INVENTION

Accordingly, one object to the present invention is to provide a compactly packaged self-inflatable rescue mask, which self-inflates when removed from the package.

Another object of this invention is to provide a mask which enables the resuscitator to deliver mouth to mask resuscitation to a victim without the risk of physical contact and contamination from communicable diseases.

Still another object of the invention is to provide a flattened and folded self-inflatable rescue mask with a novel air valve which seals the air in the inflated mask.

Another object of this invention is to provide a foldable pocket mask made of a flexible form-retaining plastic material which has sufficient resilience to seal effectively against the face of the patient. "Resilience is the property of returning to the original shape after distortion within elastic limits." Hackk's Chemical Dictionary Fourth Edition p. 578, column 2.

Still another object of this invention is to provide a disposable rescue mask.

Additional objects, advantages and novel features of the invention will be set forth in the description which follows, and in part will become apparent to those skilled in the art upon examination of the following or may be learned by practice of the invention. The objects and advantages of the insertion may be realized and attained by means of the instrumentalities and combinations particularly pointed out in the appended claims.

It has now been found that the self-inflatable rescue mask in accordance with present invention overcomes the deficiencies of prior art devices by providing a package deflated mask which can be carried in a pocket, and when removed from said package, it self-inflates into a mask which enables the rescuer to instantly deliver mouth to mask resuscitation to a victim, without endangering the resuscitator from acquiring communicable diseases, such as AIDS, etc., from the victim.

The disposable self-inflatable rescue mask for ventilation CPR (cardio-pulmonary resuscitation) comprises a dome-shaped foldable portion having around its peripheral edge an inflatable bladder provided with a built-in sealed air valve, said bladder being shaped to fit around the nose and mouth areas and effectively seal against the face, and a blow-in tube in an opening at the apex of the dome provided with a mouthpiece for delivery of expired air to the patient. Removal of said seal from the air valve automatically inflates said bladder, and the internal mask pressure seals the air in the mask, which provides a tight mask-to-face seal on the patient. A one-way valve or filter may optionally be inserted in the mouthpiece to block contact with contaminants exhaled by the patient.

The self-inflatable rescue mask may be made of a transparent flexible, form-retaining plastic material such as polyvinyl chloride, polystyrene, polyurethane and the like. It is the inherent "memory" and/or resilience of the particular material composing the bladder 12 of the instant invention which causes said bladder to assume a shape which is consistent with that of its fully inflated shape, thereby causing a pressure gradient down which ambient air flows into the bladder until a pressure equilibrium is established and the bladder is thereby fully inflated. Preferably, the dome shaped portion may be made of increased wall thickness to form increased flexure stiffness, and the bladder may be made of less wall thickness to increase the flexibility and foldability, of the deflated and flattened mask designed to fit into a carrying case and sealed for future use. The carrying case is preferably pocket size and can be easily and readily used by such groups as ambulance, paramedical and fire services, surf life-savers, police forces and also private people. The rescuer simply removes the seal from the carrying case which may simultaneously or separately open the air valve in the folded flattened mask, and remove the mask from the carrying case which self-inflates into a mask, shaped to enclose the mouth and nose and firmly seals on the face of the victim. A single closure means such as an adhesive peel-off strip may be used for both the carrying case and the air-valve simultaneously. The rescuer can immediately blow air into the mouthpiece of the mask to deliver air to the victim's mouth and nose.

The disposable self-inflatable rescue mask of this invention will be more fully described by the accompanying drawings.

DETAILED DESCRIPTION OF A PREFERRED EMBODIMENT

Figure 1:
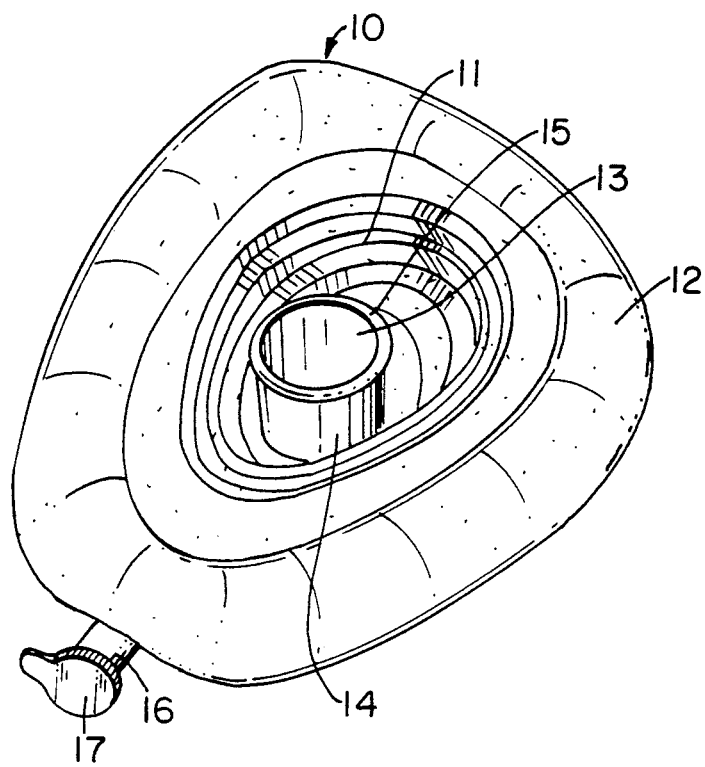
FIG. 1 is a perspective view of a deflated resuscitation mask according to the invention, ready for packaging.
Figure 2:
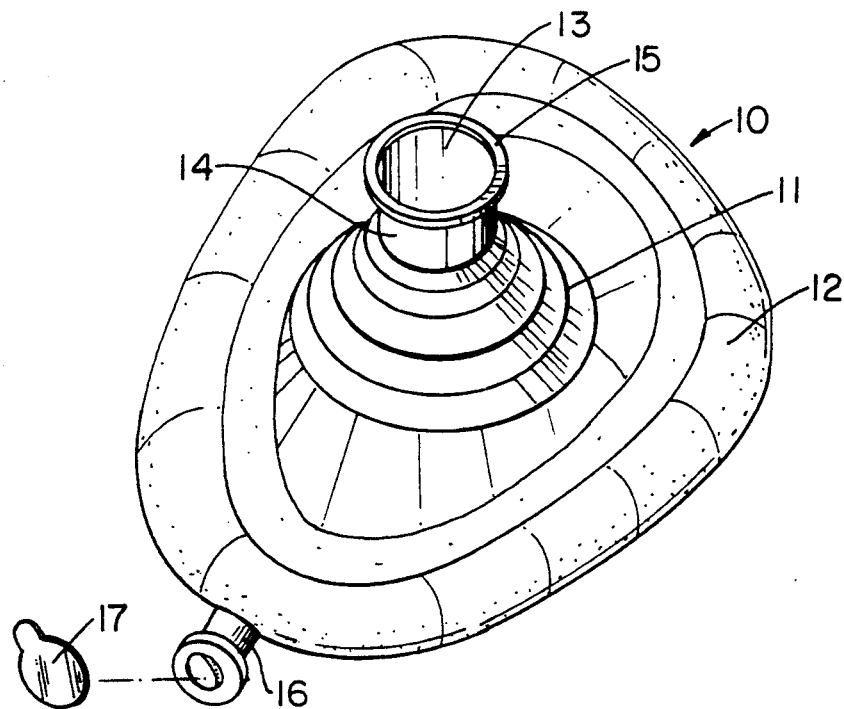
FIG. 2 is a perspective view of an inflated resuscitation mask, shown ready to use.
Figure 3:
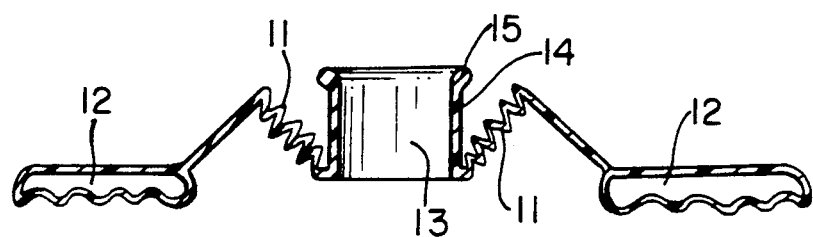
FIG. 3 is a sectional view of FIG. 1, cutting through the center of the mask.
Figure 4:
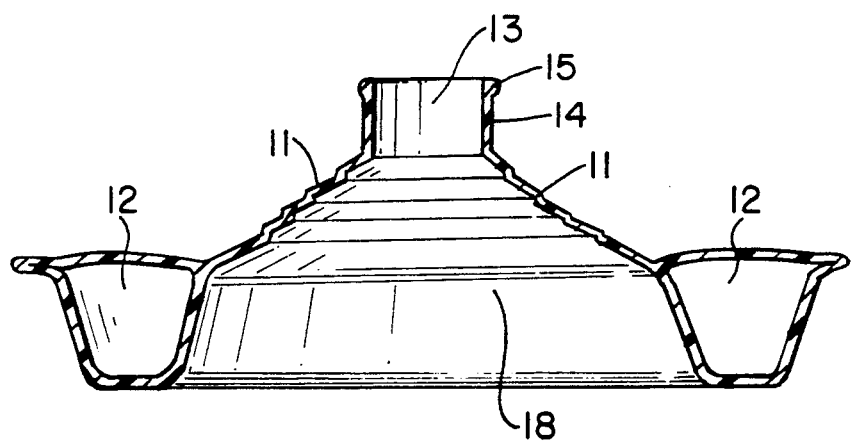
FIG. 4 is a sectional view of FIG. 2, cutting through the center of the mask.
Figure 5:
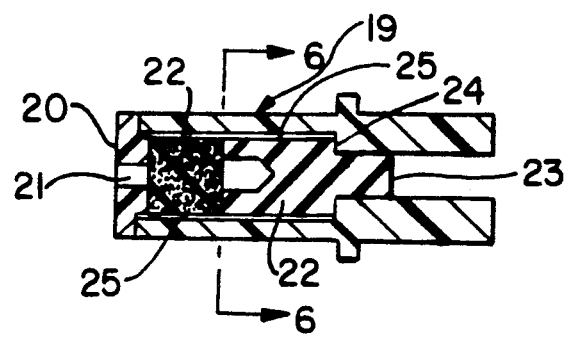
FIG. 5 is a sectional elevational view of the air pressure valve in FIGS. 1 and 2.
Figure 6:
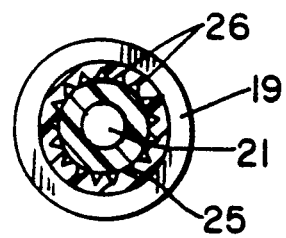
FIG. 6 is a sectional view along 6—6 of FIG. 5.

In the drawings, FIGS. 1 and 3 represent the rescue mask 10, deflated prior to packaging, which includes a foldable dome-shaped portion 11, having around its peripheral edge a deflated, inflatable bladder 12, an air-inlet opening 13, at the apex of the dome through which a blow-in tube 14, projects. The blow-in tube 14, is provided with a round or elliptical mouth piece 15. The elliptical mouthpiece is more comfortable to use because it fits the shape of the lips and mouth when blowing expired air into the inflated mask. A one-way air-valve 16, is built into the inflatable bladder 12, and sealed by means of a removable plug or a peel-off strip 17. Removal of said seal 17, opens air valve 16, and the ambient air flows into bladder 12, which automatically inflates mask 10, and the internal mask pressure seals the air in mask 10, to form the self-inflated mask, as shown in FIGS. 2 and 4. Upon removal of the seal 17, the outside pressure of the ambient air is positive, i.e. greater than the negative (lesser) pressure within the cavity of bladder 12. The pressure differential between the outside ambient air, and the pressure within the deflated bladder causes the ambient air to automatically flow into the bladder 12, until the bladder is inflated, which inflates the rescue mask 10. The pressure within the bladder 12, is negative relative to the positive (high) ambient air pressure, causing the air to flow down the pressure gradient, across the valve 16, into the bladder 12. When there is no pressure gradient, i.e. when the bladder 12 is inflated, air ceases to flow into the valve 16, and closes the valve 16, due to the forces within the system.

The dome-shaped mask 10, as shown in FIGS. 1 and 2, is designed to fit around the mouth and nose areas and effectively seal against the face. The inflation of the bladder 12, and the unfolding of the dome-shaped portion 11, provides a mask which encloses the mouth and nose and seals against the patient's face, forming a plenum chamber 18, filled with air blown therein by the rescuer. This space within the enclosed chamber 18, provides a sufficient distance between the rescuer's mouthpiece 15, and the patient's mouth and nose, to protect the rescuer from contact with the patient and the patient's exhaled fluids. A one-way valve or filter may optionally be placed in the rescuer's mouthpiece 15, to provide additional protection against contact with patient's exhaled fluids.

The air valve 16, shown in FIGS. 5, 6, 7 and 7a, is a plastic body 19 connected to the interior of bladder 12, comprising a plastic cap 20, provided with an opening 21, for the flow of air into the bladder. A light open sponge cell 22 supplies a light push with a plunger 23, to keep the valve seated 24. The dome-shaped portion 11 may be made of silicone rubber or surgical latex. The bladder 12 may be made of any flexible, elastic material which has memory to assume a particular shape. Negative pressure within the bladder occurs when the bladder is deflated and sealed due to the inherent memory of the material. This negative pressure is necessary to create air-flow into the bladder when the valve is unsealed. The air valve 16 is provided with axial serrations 26, for air passages 25. Open air valve 16, is provided with a sealing means such as a plug 27, or an adhesive peel-off seal 28 to close the air valve 16, and prevent air flow into the bladder 12.

The pressure within the bladder 12, plus the sponge pressure 22, which pushes the valve plunger 23, to seal the opening 21, into the bladder 12, when the pressure is equalized, the air valve is sealed after the bladder is inflated, and the internal mask pressure seals the air in the mask to form the self-inflated mask.

Figure 7:
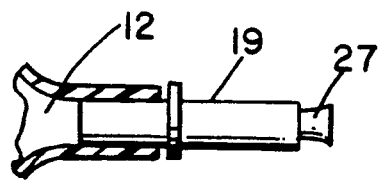
FIG. 7 is a side elevational view of the sealed air valve in the deflated mask ready for packaging.
Figure 7A:
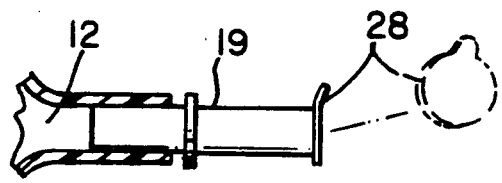
FIG. 7a is a side elevational view of an alternate means of sealing the air valve in a deflated mask ready for packaging.

The deflated inflatable mask can be manually or self-inflated by inflating the bladder 12, to assume the shape of the rescue mask 10, by blowing air into the open air-valve 16 or the outside positive ambient air flows per se into the open air valve, which overcomes the sponge pressure; and the internal mask pressure, which is greater than atmospheric pressure, seals the air in the mask automatically. The inflated mask can be deflated by pushing a blunt rod into the open air-valve 16, and the mask is squeezed to deflate, and then the open air-valve 16 is sealed with a plug 27, or an adhesive peel-off seal 28, or other sealing means. The sealed air valve in the deflated mask 10, prevents the flow of air into the bladder 12 and the mask is now flattened and folded and ready for packaging, as shown in FIGS. 7 and 7A.

Figure 8:
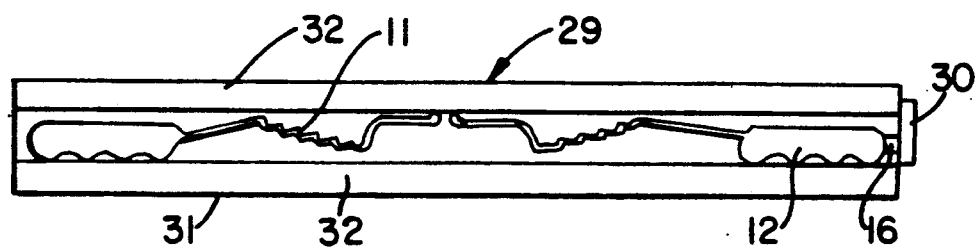
FIG. 8 is a sectional view of a compact container containing the flattened deflated mask of present invention.

The mask is packaged in a carrying case comprising two similar parts to form a container which is shaped to receive said deflated mask in a flattened and folded state and sealed with a closure means. As shown in FIG. 8, carrying case 29, comprises two similar parts 32, shaped to receive the deflated, folded and flattened mask 10, and sealed with a closure means 30. The sealed package 29 can be carried safely on one's person, and requires little space, such as in a pocket. The air valve 16 in the deflated mask 10 is sealed with a plug 27, or a peel-off seal 28, or other adaptable closure means prior to packaging the folded and flattened mask in carrying case 29, which is closed with an adhesive peel-off seal 30, or tear strip 31, or other suitable closure means. The adhesive seal 30, or tear strip 31, is removed upon opening the packaged case 29, and after the plug 27 is removed from the air valve 16, in the deflated bladder 12; said rescue mask 10 self-inflates, and is ready to be placed on the patient's face to provide instant resuscitation. The adhesive seal 30 on the packaged case 29, may provide a dual closure function of sealing both the air valve 16, simultaneously with the case 29. This type of closed packaged case 29, eliminates the step of removing the seal from the air valve, which provides faster action in emergencies. Upon opening the package with the dual sealing function, it provides an instant self-inflatable mask for instant use. This is of particular importance in emergency or critical situations where immediate resuscitation of victims is required.

It is understood that the foregoing detailed description is given merely by way of illustration, and that variations may be made therein without departing from the spirit of the invention. The "Abstract" given above is merely for convenience of technical searches and is not to be given any weight with respect to the scope of the invention.

I claim:

1. A compactly packaged deflated self-inflatable rescue mask which self inflates when removed from the package, comprising a flexible form-retaining plastic dome shaped foldable portion having around its peripheral edge an inflatable bladder composed of plastic material which has sufficient resilience to cause said bladder to assume a shape which is consistent with its fully inflated shape, thereby causing a pressure gradient down which ambient air flows into the bladder until a pressure equilibrium is established, and the bladder is thereby fully inflated, said bladder is provided with a built-in, sealed air-valve, wherein said seal is removed from said air valve to automatically inflate said bladder, which allows the ambient air to flow into the inflatable bladder and seals the air in the inflated mask which retains its shape firmly, said bladder being shaped to fit around the nose and mouth, and a blow-in tube is disposed in an opening at the apex of the dome, provided with a mouthpiece for delivery of the rescuer's expired air to the patient.

2. The mask according to claim 1, packaged in a carrying case comprising two similar parts to form a container which is shaped to receive said mask in a deflated, flattened and folded state, and sealed with a closure means.

3. The mask according to claim 1, wherein removal of the seal from the air valve which causes the positive pressure of the ambient air to flow into the bladder which automatically inflates the bladder, and the internal mask pressure seals the air in the mask which forms the self-inflated mask ready for use on the patient.

4. The mask according to claim 3, wherein the inflation of the bladder and the unfolding of the dome-shaped position provides a mask which encloses the mouth and nose and seals against the patient's face, forming a plenum chamber filled with air blown therein by the rescuer.

5. The mask according to claim 4, wherein the space within the enclosed plenum chamber provides a sufficient distance between the rescuer's mouthpiece and the patient's mouth and nose, to protect the rescuer from contact with the patient's exhaled fluids.

6. The mask according to claim 2, wherein removal of the closure means from the carrying case and the seal from the air valve opens the air valve in the folded flattened mask, which self-inflates into a mask shaped to enclose the mouth and nose which firmly seals on the face of the patient.

7. The mask according to claim 2, wherein a single closure means is used for both the carrying case and the air-valve simultaneously.

8. The mask according to claim 7, wherein the single closure means is an adhesive peel-off seal.

9. The mask according to claim 1, wherein a one-way valve is inserted into the mouthpiece.

10. The mask according to claim 1, wherein the air valve connected to the bladder is provided with air passages and an opening for the flow of air into the bladder which automatically inflates, and the internal mask pressure which is greater than atmospheric pressure seals the air in the mask automatically.

11. The mask according to claim 3, wherein the self-inflated mask enables the rescuer to instantly deliver mouth to mask resuscitation to a victim.

12. The mask according to claim 2, wherein the rescuer simply removes the seal from the carrying case which may simultaneously or separately open the air valve in the folded flattened mask, and remove the mask from the carrying case which self-inflates into a mask shaped to enclose the mouth and nose, and firmly seals on the face of the victim, and the rescuer immediately blows air into the mouthpiece of the mask to deliver air to the victim's mouth and nose.

13. A disposable self-inflatable foldable pocket rescue mask, for ventilation CPR, made of a flexible form-retaining plastic material which has sufficient resilience to seal effectively against the face of the patient, comprising a form-retaining dome-shaped portion, having around its peripheral edge an inflatable bladder made of a flexible elastic material which has sufficient resilience which causes said bladder to assume a shape which is consistent with that of its fully inflated shape, and provided with a built-in air valve provided with a seal, an air-inlet opening at the apex of the dome through which a blow-in tube projects, provided with a round or elliptical mouthpiece for delivery of the rescuer's expired air to the patient, removal of the seal from the air valve opens said air valve, and the outside pressure of the ambient air being greater than the pressure within the cavity of the bladder causes the ambient air to flow into the bladder which automatically inflates the mask, and the internal mask pressure seals the air in the mask to form the self-inflated mask.

14. The mask according to claim 13, wherein the inflated bladder encloses the mouth and nose, and seals against the patient's face, and the dome shaped portion forms a plenum chamber filled with air blown therein by the rescuer.

15. The mask according to claim 13, wherein said air valve is a one-way air valve which automatically allows the ambient air to flow into the bladder due to the pressure differential until the internal pressure of the bladder plus the sponge within the valve closes the valve automatically.

16. The mask according to claim 13, wherein the form-retaining inflatable bladder is provided with a built-in air valve which allows the ambient air to flow into the inflatable bladder and self-seals the air in the self-inflated mask which retains its shape firmly.

17. A self-inflatable rescue mask made of a flexible form-retaining plastic material which has sufficient plastic material which has sufficient resilience to effectively seal against the patient's face, comprising a form-retaining dome-shaped portion, having around its peripheral edge, an inflatable bladder composed of resilient material which causes said bladder to assume a shape which is consistent with that of its fully inflated shape thereby causing a pressure gradient down which ambient air flows into the bladder until a pressure equilibrium is established and the bladder is thereby fully inflated, said bladder is provided with a built-in, one-way, air valve, which seals the air in the inflated bladder, and an air inlet at the apex of said dome is provided with a blow-in tube provided with a round or elliptical mouthpiece for delivery of rescuer's expired air to the patient.

* * * * *